US00PP35079P2

(12) United States Plant Patent
Werner et al.

(10) Patent No.: US PP35,079 P2
(45) Date of Patent: Apr. 4, 2023

(54) ***CERCIS* PLANT NAMED 'NC2014-5'**

(50) Latin Name: *Cercis canadensis*
Varietal Denomination: NC2014-5

(71) Applicant: North Carolina State University, Raleigh, NC (US)

(72) Inventors: Dennis Werner, Raleigh, NC (US); Leanne M. Kenealy, Durham, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/968,087

(22) Filed: Oct. 18, 2022

Related U.S. Application Data

(60) Provisional application No. 63/257,239, filed on Oct. 19, 2021.

(51) Int. Cl.
*A01H 6/00* (2018.01)
*A01H 5/02* (2018.01)

(52) U.S. Cl.
USPC ..... Plt./216

(58) Field of Classification Search
USPC ..... Plt./216
CPC ..... A01H 6/00; A01H 5/02
See application file for complete search history.

(56) References Cited

U.S. PATENT DOCUMENTS

PP15,854 P2 7/2005 Woody
PP17,161 P3 10/2006 Woody

*Primary Examiner* — Keith O. Robinson
(74) *Attorney, Agent, or Firm* — Panitch Schwarze Belisario & Nadel LLP; Stephany G. Small; Travis Bliss

(57) ABSTRACT

A new and distinct variety of *Cercis* plant, referred to by its cultivar name, 'NC2014-5', is disclosed. The new variety is characterized by its profusion of light-purplish-pink-colored flowers. Small, green colored foliage which aligns in an attractive overlapping pattern along the stem is formed and moderately slow growing, upright, dwarf growth habit is displayed.

3 Drawing Sheets

Latin name of genus and species of plant claimed: *Cercis canadensis.*

Variety denomination: 'NC2014-5'.

BACKGROUND OF THE INVENTION

The present invention relates to a new and distinct cultivar of *Cercis* plant botanically known as *Cercis canadensis* and hereinafter referred to by the cultivar name 'NC2014-5'.

The new cultivar originated in a controlled breeding program in Jackson Springs, N.C. in 2010.

The new *Cercis* cultivar is the result of a controlled cross wherein two parents were crossed which previously had been studied in the hope that they would contribute the desired characteristics. The female parent (i.e., the seed parent) of the new cultivar was *Cercis* 'Texas White', not patented. The male parent (i.e., the pollen parent) of the new cultivar is *Cercis* 'Ace of Hearts', U.S. Plant Pat. No. 17,161.

The parentage of the new variety can be summarized as follows:

'Texas White' x 'Ace of Hearts'

The seeds resulting from the above pollination were sown and small plants were obtained which were physically and biologically different from each other. Selective study in 2014 in a controlled environment in Jackson Springs, N.C. resulted in the identification of a single plant of the new variety, which was selected for its profusion of light purplish-pink colored flowers, small green and attractive overlapping leaf arrangement, and upright dwarf growth habit.

The new variety has been found to undergo asexual propagation in in Belvidere, Tenn. since 2015 by chip budding. This asexual reproduction has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'NC2014-5' as a new and distinct cultivar of *Cercis* plant:

(a) Profusion of light purplish-pink-colored flowers,
(b) Small, green-colored foliage which aligns in an attractive overlapping pattern along the stem; and
(c) Moderately slow growing, upright, dwarf growth habit.

The new variety of the present invention can readily be distinguished from its ancestors. More specifically, plants of 'Texas White' (i.e., the seed parent) display white-colored flowers and exhibits a rounded habit, whereas plants of the new variety display light purplish-pink-colored flowers and exhibit an upright, dwarf growth habit. In addition, plants of 'Ace of hearts' (i.e., the pollen parent) display more purple-colored flowers, whereas plants of the new variety display more purplish-pink colored flowers and exhibit a more upright habit compared to plants of the pollen parent.

Moreover, the new variety can be readily distinguished from other similar non-parental varieties. Of the many commercially available *Cercis* cultivars, the most similar in comparison to the new cultivar is 'Little Woody', U.S. Plant Pat. No. 15,854. However, plants of the new cultivar differ from plants of 'Little Woody' in at least the following characteristic:

1. Plants of the new cultivar have less textured leaves than plants of 'Little Woody'.
2. Plants of the new cultivar have a more upright growth habit than plants of 'Little Woody'.

BRIEF DESCRIPTION OF THE PHOTOGRAPHS

The accompanying photographs show, as nearly true as it is reasonably possible to make the same in color illustrations of this type, typical growth habit, flowering and foliage characteristics of the new cultivar. Colors in the photographs differ slightly from the color values cited in the detailed description, which accurately describes the colors of 'NC2014-5'. The plants in the photographs were approximately four years old and were growing in a test field in Cochranville, Pa.

DETAILED BOTANICAL DESCRIPTION

Figure 1:
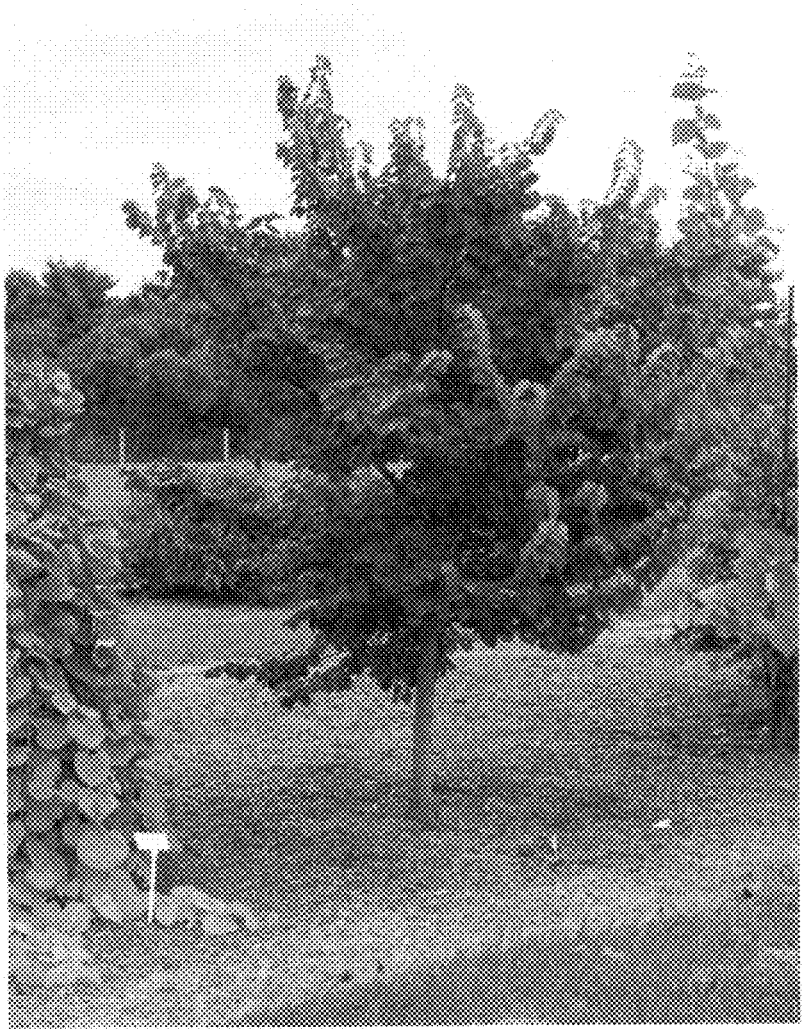
FIG. 1 illustrates a side view of 'NC2014-5'
Figure 2:
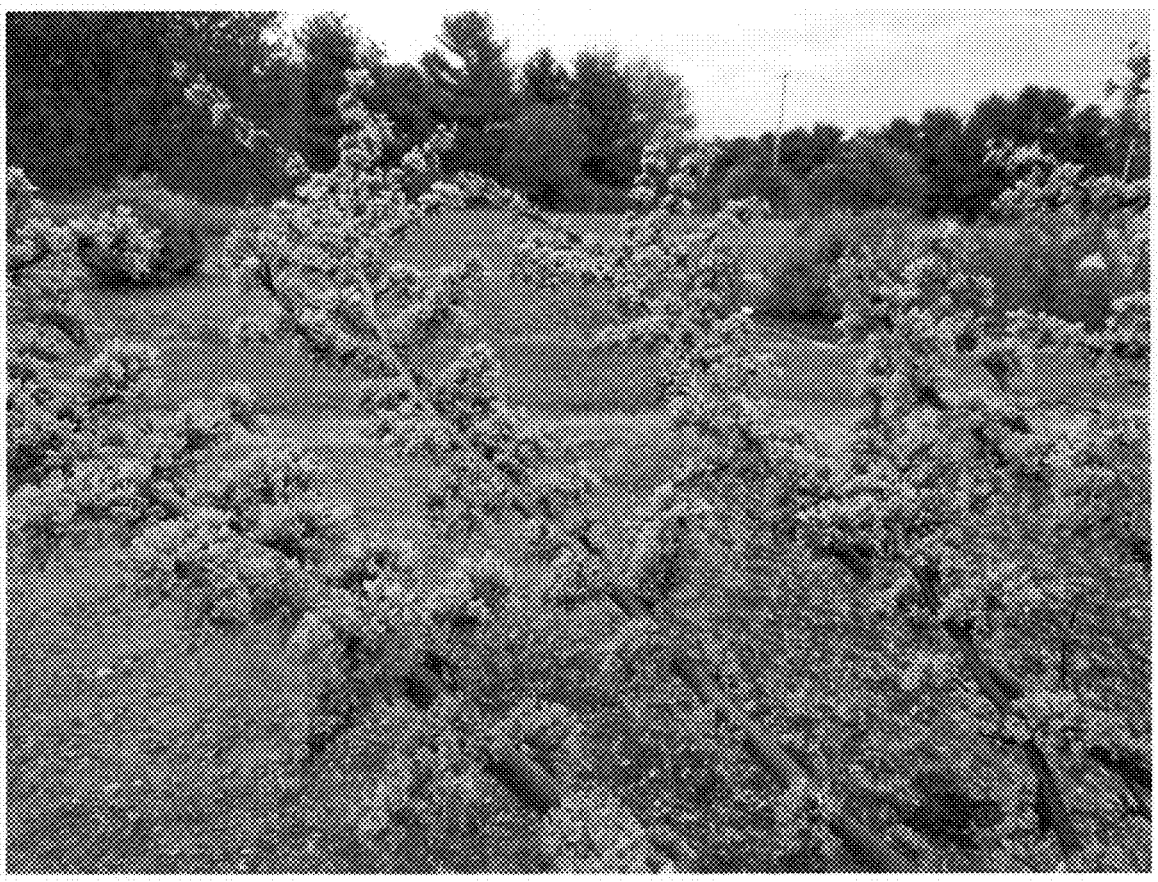
FIG. 2 illustrates flowering of 'NC2014-5'
Figure 3:
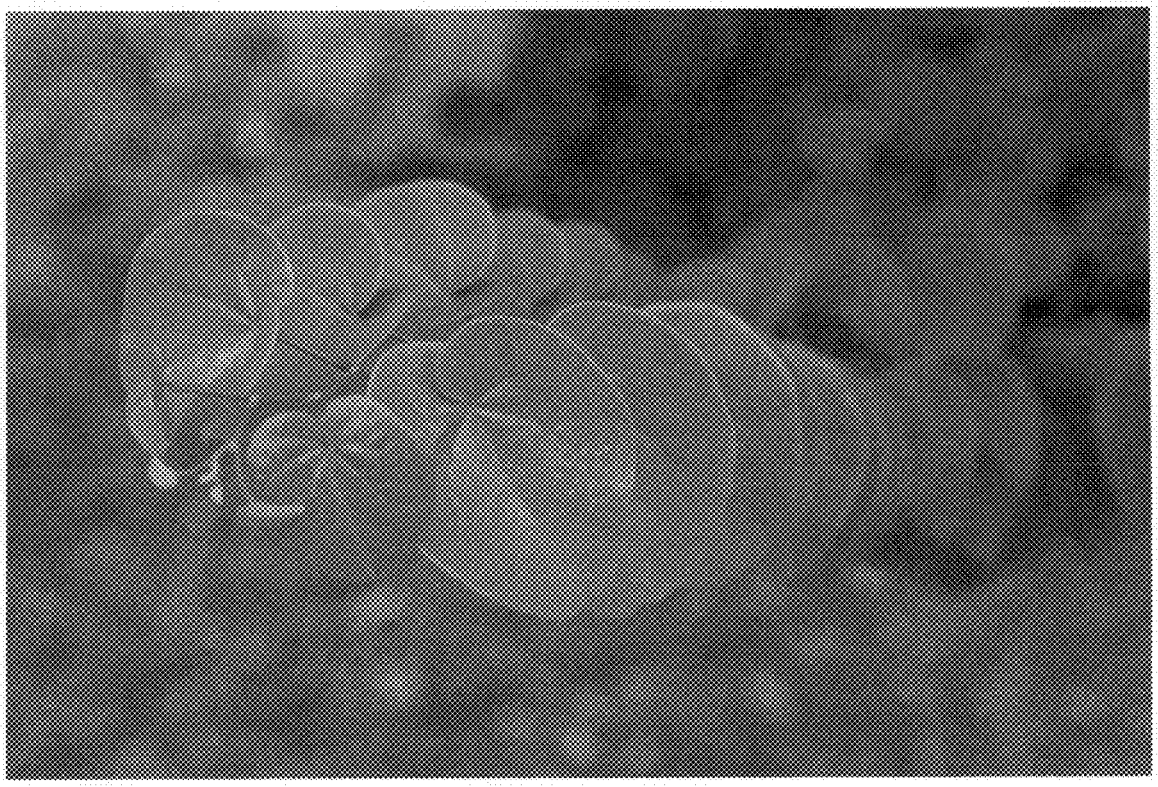
FIG. 3 illustrates a close-up view of the foliage of 'NC2014-5'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values of the flowers were determined in spring 2019. Color values of the foliage were determined in summer 2019 under natural light conditions in Jackson Springs, N.C.

The following descriptions and measurements describe plants produced from chip budding and grown outside in Jackson Springs, N.C. Plants were approximately four years of age. Measurements and numerical values represent averages of typical plants.

Botanical classification: *Cercis canadensis* cultivar NC2014-5.

Parentage:

*Female parent.*—*Cercis* 'Texas White', not patented.

*Male parent.*—*Cercis* 'Ace of Hearts', U.S. Plant Pat. No. 17,161.

Propagation:

*Type.*—Chip budding.

Plant description:

*Type.*—Deciduous perennial tree.

*Growth habit and general appearance.*—Moderately slow growing, upright, dwarf tree.

*Commercial crop time.*—Approximately 1.5 years from budding to finish as a 2 to 3-foot tree.

*Size.*—Height of 4-year old tree: Approximately 1.4 meters. Width: Approximately 76.2 cm.

*Trunk.*—Texture: slightly rough. Color: 201B.

*Branches.*—Densely branched. Strength: Moderately strong. Diameter of one-year old growth: Approximately 4.0 mm. Internode length: 2.1 cm on average. Growth pattern: slightly zigzag, deviating less than 5 degrees from vertical at each node. Texture of new growth: Slightly rugose. Color of young stem: N77A to 200C when hardened off. Color of mature stem: previous seasons growth is N199B. Lenticel: numerous, tiny. Lenticel length: Less than 1.0 mm. Lenticel shape: circular to slightly elongate. Lenticel color: 164B.

Foliage description:

*General description.*—Type: Deciduous. Arrangement: Alternate.

*Leaves.*—Shape of immature leaves: Suborbicular. Shape of mature leaves: broad-ovate. Apex: Moderately to distinctly pointed. Base: Cordate. Margin: Entire. Length to base of sinus: Approximately 5.1 cm. Length to end of lobe: Approximately 6.5 cm. Sinus indentation: Approximately 1.2 cm. Width: Approximately 6.0 cm. Texture of upper and lower surfaces: Smooth, glabrous. Venation pattern: Reticulate. Color of upper surface of mature foliage: N137A with indistinguishable venation. Color of lower surface of mature foliage: N138B with indistinguishable venation. Fragrance: None detected.

*Petiole.*—Length: Approximately 2.6 cm. Diameter: Approximately 1.0 mm. Texture: Smooth, glabrous. Color: 144A.

Flowering description:

*Flowering season.*—Flowers in early spring for about 2-3 weeks depending on weather conditions.

*General description.*—Form: Fasicle. Flower Arrangement: Sessile clusters. Symmetry: Bilateral symmetry. Type: Papilionaceous. Quantity per cluster: 6 per cluster on average. Flower length: 8.0 mm on average. Flower width across wings at anthesis: 5.0 mm on average. Flower depth (bottom of keel petals to top of wings): 2.0 mm on average.

*Bud just before opening.*—Shape: slightly elongate. Diameter: Approximately 1.0 mm. Length: Approximately 1.0 mm. Color: 59B. Texture: Glabrous.

*Petals.*—Quantity: 5, unfused. Texture of upper and lower surfaces: Glabrous. Color of banner, wings, and keel base when first and fully open: 73B. Color of keel tip when first and fully open: 61B.

*Calyx.*—Shape: vase-shaped. Diameter: Approximately 2.0 mm at top of hypanthium. Length: Approximately 3.0 mm. Color of outer and inner surfaces: 59C. Texture of inner and outer surfaces: Glabrous.

*Sepals.*—Arrangement: Fused.

*Pedicel.*—Strength: Strong. Shape: Round. Length: Approximately 0.4 cm. Diameter: Less than 1.0 mm. Texture: Glabrous. Color: 60C.

*Reproductive organs.*—Androecium: Stamen quantity per flower: 10 on average, unfused. Stamen length: 6.0 mm. Stamen width: Less than 1.0 mm. Anther shape: Round. Anther color: 65A. Filament length: Less than 1.0 mm. Filament width: Less than 1.0 mm. Filament color: 65A. Pollen amount: Sparse. Pollen color: 11B. Gynoecium: Pistil length: Approximately 4.4 mm on average. Pistil width: Less than 1.0 mm. Pistil texture: Glabrous. Stigma shape: Round. Stigma color: 59D. Stigma length: Less than 1.0 mm. Stigma width: Less than 1.0 mm. Style shape: round. Style width: Less than 1.0 mm. Style color: 65A. Ovary position: Superior. Ovary shape: Elongate. Ovary length: Less than 1.0 mm. Ovary width: Less than 1.0 mm. Ovary color: 59A.

*Seed production*.—None observed to date.

*Disease and pest resistance*.—Plants of the new *Cercis* have not been noted to be resistant to pathogens and pests common to *Cercis*.

We claim:

1. A new and distinct cultivar of *Cercis* plant named 'NC2014-5', substantially as herein illustrated and described.

* * * * *